United States Patent [19]

Johnson et al.

[11] Patent Number: 5,106,844
[45] Date of Patent: Apr. 21, 1992

[54] IMIDAZO[2,2-B][3]BENZAZEPINE AND PYRIMIDO[2,1-B][3]BENZAZEPINE ANTIARRHYTHMIC AGENTS

[75] Inventors: Robert E. Johnson, East Greenbush; Carl A. Busacca, Ghent, both of N.Y.

[73] Assignee: Sterling Drug Inc., New York, N.Y.

[21] Appl. No.: 757,088

[22] Filed: Sep. 10, 1991

[51] Int. Cl.$^5$ .................. A61K 31/55; C07D 487/04
[52] U.S. Cl. .................................... 514/217; 540/551
[58] Field of Search ....................... 540/551; 514/217

[56] References Cited

PUBLICATIONS

Johnson et al., "J. Het. Chem", vol. 2, No. 1, pp. 26-36 (1965).
Wendelin, W. et al., "Bridged Derivatives of Phenylethylamines and Nitrogen Analogous Compounds. Part 2. Synthesis and Pharmacological Activities of 4-5-Dihydro-1H-3-Benzazepines and Fused Derivatives" Sci. Pharm. 57:27-38 (1989).
Vejdelek, Z. and Protiva, M., "Synthesis of Some Derivatives of 1-Phenyl-2,3,4,5-Tetrahydro-1H-3-Benzazepine and 11-Phenyl-5,6-Dihydro-11H-S--Triazolo[3,4-b]-3-Benzazepine" Collect. Czech. Chem. Commun. 55:2345-2350 (1990).

Primary Examiner—Robert T. Bond
Attorney, Agent, or Firm—Paul Dupont

[57] ABSTRACT

Novel imidazo[2,1-b][3]benzazepines and pyrimido[2,1-b][3]benzazepines of formula I, pharmaceutical compositions containing them, methods for treating cardiac arrhythmia in mammals utilizing them, and processes for synthesizing them.

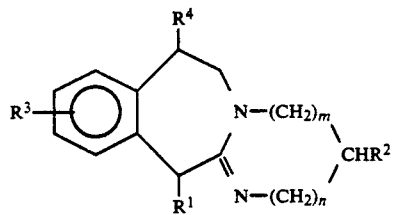

17 Claims, No Drawings

IMIDAZO[2,2-B][3]BENZAZEPINE AND PYRIMIDO[2,1-B][3]BENZAZEPINE ANTIARRHYTHMIC AGENTS

BACKGROUND OF THE INVENTION

1. Field of the Invention

The present invention relates to novel imidazo[2,1-b][3]-benzazepines and pyrimido[2,1-b][3]benzazepines, to pharmaceutical compositions containing them, and to methods for treating cardiac arrhythmias in mammals utilizing them.

2. Information Disclosure Statement

Published examples of imidazo[2,1-b][3]benzazepines or pyrimido [2,1-b][3]benzazepines are unsubstituted. Wendelin et al. [Sci. Phar. 57. 27-38 (1989)]disclose 2,5,6,11-tetrahydro-3H-imidazo[2,1-b][3]benzazepine and 2,3,4,6,7,12-hexahydropyrimido[2,1-b][3]benzazepine.

Vejdelek and Protiva [Coll. Czech. Chem. Comm. 55, 2345-2350 (1990)]disclose 6,11-dihydro-3-methyl-11-phenyl-5H-1,2,4-triazolo[3,4-b][3]benzazepine and 9-chloro-6,11-dihydro-3-methyl-11-phenyl-5H-1,2,4-triazolo[3,4-b][3]benzazepine. No utility is disclosed.

SUMMARY OF THE INVENTION

In a product aspect, the invention relates to imidazo-[2,1-b][3]benzazepines and pyrimido[2,1-b][3]benzazepines of formula I

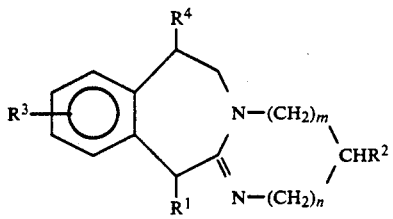

wherein
- $R^1$ is phenyl, naphthyl, thienyl, phenyl substituted with one or two substituents chosen independently from the group consisting of lower-alkyl, lower-alkoxy and halogen, or $R^1$ is hydrogen when $R^4$ is phenyl or substituted phenyl;
- $R^2$ is hydrogen or phenyl;
- $R^3$ is one or two substituents chosen independently from the group consisting of hydrogen, lower-alkyl, lower-alkoxy and halogen;
- $R^4$ is hydrogen; or, when $R^1$ is hydrogen, $R^4$ is phenyl or phenyl substituted with lower-alkyl, lower-alkoxy or halogen;
- m and n are each zero, one or two and the sum of m plus n is one or two.

Preferred compounds are those wherein $R^2$ and $R^3$ are hydrogen and $R^1$ is phenyl.

In a composition aspect, the invention relates to compositions for the treatment of cardiac arrhythmia which comprise compounds of formula I together with pharmaceutical In a method aspect, the invention relates to a method for the treatment of cardiac arrhythmia which comprises administering an antiarrhythmically effective amount of a compound of formula I.

In a process aspect, the invention relates to a process for preparing compounds of formula I which comprises cyclizing Compounds of formula III

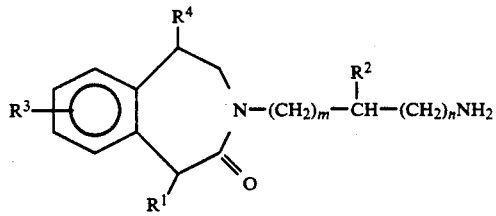

Lower-alkyl as used herein describes linear, branched, or cyclic saturated carbon chains of six or fewer carbon atoms; lower-alkoxy as used herein describes linear or branched alkoxy substituents containing six or fewer carbon atoms; halogen describes bromine, chlorine or fluorine.

In the text that follows, the substituents R are defined when initially presented and maintain that definition whenever they occur subsequently.

DETAILED DESCRIPTION INCLUSIVE OF PREFERRED EMBODIMENTS

The compounds of the invention may be synthesized from 3-benzazepine-2-ones by alkylation with a protected, masked, or free aminoethyl or aminopropyl halide, followed by deprotection or unmasking of the amine and dehydrative cyclization:

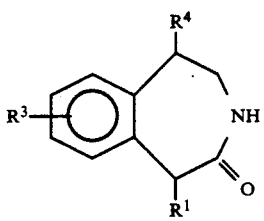

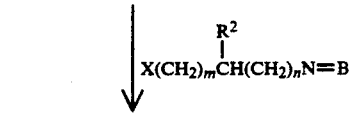

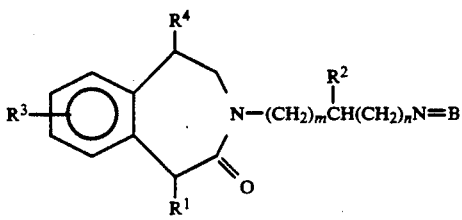

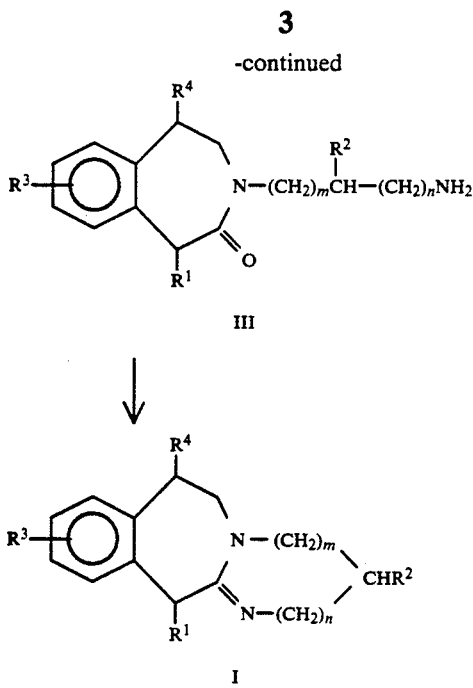

N=B is amino, phthalimido or dibenzylamino; or when n is one or two, $(CH_2)_n$-N=B may be $(CH_2)_{n-1}CN$;

X is chlorine or bromine.

The benzazepinone is reacted with the halide in the presence of a base such as sodium hydride in DMF or preferably butyllithium in THF in the presence of 1,3-dimethyl-3,4,5,6-tetrahydro-2(1H)-pyrimidinone(N,N'-dimethylpropyleneurea=DMPU). When 3-aminopropyl is to be added (i.e. m+n=2), the phthalimide may be used; when 2-aminoethyl is to be added, one of the other amino-equivalents must be used because the phthalimide undergoes HX elimination rather than alkylating the benzazepine. The precursor to compounds where m+n=2 and $R^2$=H may also be made by condensing the benzazepinone with acrylonitrile in the presence of Triton B. The phthalimide is deprotected with hydrazine, the nitrile is reduced in the presence of palladium, or the benzyl protecting groups are cleaved by hydrogenolysis. The free primary amine is then dehydratively cyclized in an azeotroping solvent, optionally in the presence of a catalytic amount of an acid such as p-toluenesulfonic acid (pTSA).

The benzazepinones (II) wherein $R^4$ is hydrogen are available by syntheses known in the art. See Hamon ["Synthesis of 1-phenyl-3-benzazepines and 8-oxo-13-phenylberbine from 1-benzylisoquinolines", Ann. Chim., 10, 213-242 (1965)]and Vejdelek and Protiva (op cit.).

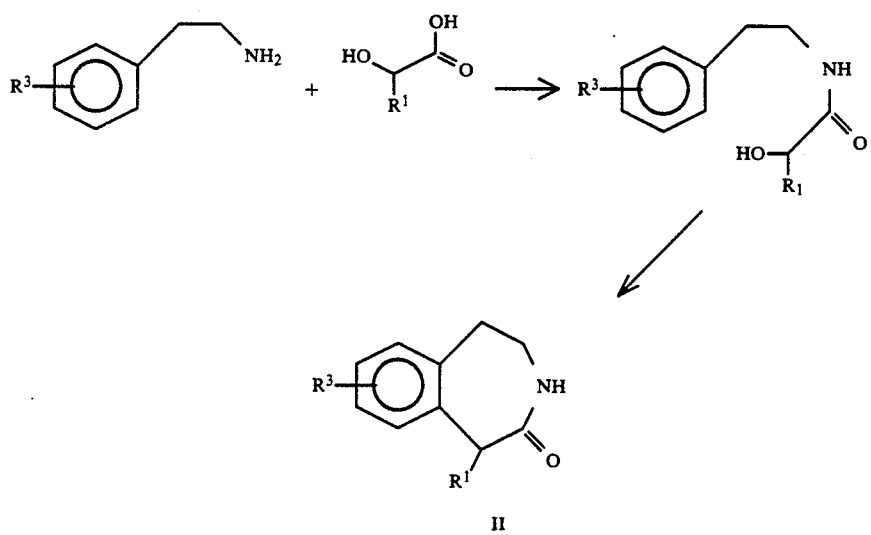

A suitable substituted phenethylamine is reacted with an α-hydroxyacid to produce an α-hydroxy amide which is cyclized in polyphosphoric acid to the benzazepinone.

The benzazepinones of formula II wherein $R^1$ is hydrogen and $R^4$ is phenyl or substituted phenyl may be synthesized by the following route:

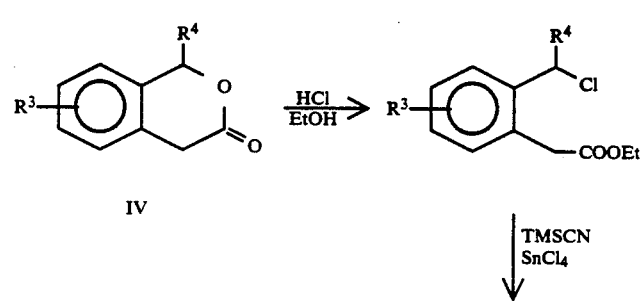

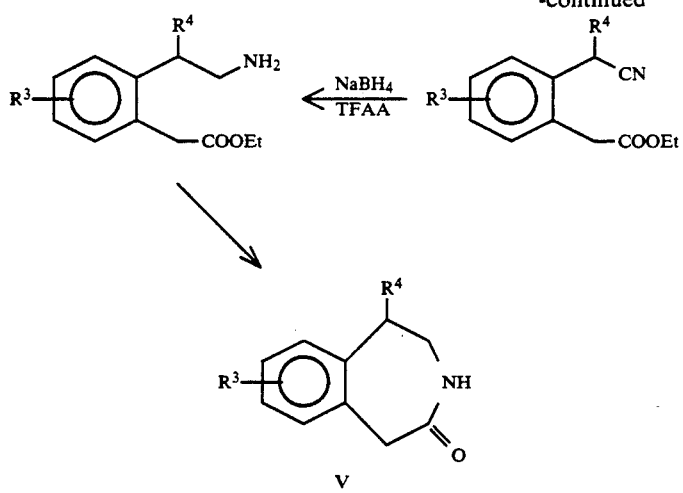

A lactone of formula IV, available via the method of U.S. Pat. No. 3,557,147, is treated with HCl gas in a lower-alkanol, preferably ethanol, and the resulting benzyl chloride is reacted with trimethylsilyl cyanide (TMSCN) in the presence of a Lewis acid, preferably stannic chloride. The nitrile is reduced with trifluoroacetoxy borohydride (prepared from sodium borohydride and trifluoroacetic acid (TFAA) and the resulting amine-ester is cyclized by refluxing in a suitable azeotroping solvent, preferably toluene.

It will be noted that compounds of the invention are asymmetric at the point of attachment of $R^1$, $R^2$ and $R^4$ when these groups are other than hydrogen. In some cases there may be an advantage to using one or the other enantiomer for the treatment of arrhythmia. Single enantiomers may be synthesized from chiral starting materials or the racemates may be resolved by methods well known in the art, such as chromatography on chiral media or recrystallization of diastereomeric salts.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC). The starting materials are either commercially available or may be prepared by procedures well known in the art.

In the following procedures, melting points are given in degrees C and are uncorrected.

In the examples which follow, Me is methyl, Et is ethyl, Ph is phenyl, Bzl is benzyl, Bu is butyl, OAc is acetyl, THF is tetrahydofuran, hex is hexane, IPA is isopropylamine, DMF is dimethylformamide, TMS is trimethylsilyl, PPA is polyphosphoric acid, MTBE is methyl t-butyl ether, DMPU is dimethylpropyleneurea.

EXAMPLE 1

4,5-tetrahydro-3(2H)-benzazepin-2-one (II: $R^1$=Ph, $R^3$=$R^4$=H)

A suspension of 31.4 mL of phenethylamine (0.25 mol) and 42.6 g of DL-mandelic acid (0.28 mol, 1.12 eq.) in 600 mL of xylenes was heated to reflux with a Dean-Stark water separator for 8 hr. The reaction was cooled, and the xylenes removed in vacuo. The resulting residue was partitioned between saturated NaHCO$_3$ and CH$_2$Cl$_2$. The CH$_2$Cl$_{12}$ layer was dried (Na$_2$SO$_4$) and the solvents removed to yield a solid which was recrystallized from THF to yield, after drying, 56 g of hydroxyamide (88%) as a white, crystalline solid, mp 95°-96° (Lit 97°-98°) To 350 g of PPA at 25° was added 30.7g of this solid (120 mmol) with mechanical stirring. The reaction was heated to 65° for 2 hr, then poured onto ice in a 4L beaker. The resulting suspension was stirred vigorously, the solids pulverized under H$_2$O and filtered, washing well with H$_2$O. Drying of the solid in vacuo and recrystallization from absolute EtOH provided 27 g of 1-phenyl-1,3,4,5-tetrahydro-3(2H)-benzazepin-2-one (95%) as a white solid, mp 189°–191°.

EXAMPLE 2

11-Phenyl-2,3,6,11-tetrahydro-5H-imidazo[2,1-b][3]benzazepine (I: $R^1$=Ph, $R^2$=$R^3$=$R^4$=H, m=1, n=0)

A suspension of 4.00 g of benzazepinone from Example 1 (16.8 mmol) in 40 mL of dry THF was cooled to 0° under N2 and treated dropwise with 7.4 mL of 2.5 M n-BuLi (18.5 mmol, ~1.1 eq.) to give a clear, pale yellow solution. After 15 the free base derived from 5.98 N,N-dibenzylchloroethylamine hydrochloride (20.2 mmol, 1.2 eq.). The bath was allowed to warm to 25°, 0.7 g of KI (~4 mmol, ~0.25 eq.) was added, and the reaction heated for 16 hr at 75°. The mixture was cooled to 25°, quenched with 8 mL of saturated NH4Cl, and the THF removed in vacuo. The residue was diluted with 150 mL of 2N NaOH causing formation of a white precipitate which was filtered, washed with H2O and placed in a vacuum oven. The filtrate was extracted with Et2O (3×125 mL), the Et2O layers extracted with 2N HCl (2×300 mL), basified (NH4OH), and again extracted with Et2O (3 ×300 mL). The Et2O was washed with H2O, saturated NaCl, dried (MgSO4), and the solvents removed to yield 2.90 g of a yellow solid. This solid was triturated with Et2O releasing a white solid which was placed in a vacuum oven. The combined yield of 3-[2-[bis(phenylmethyl)amino]ethyl]-1-phenyl-1,3,4,5-tetrahydro-3(2H)benzazepin-2-one was 4.10 g (53%) as a white solid, mp 149°–150°.

A suspension of 2.70 g of the dibenzylamino compound (5.86 mmol) in 90 mL of MeOH was cautiously treated with 1.35 g of 10% Pd/C and heated to reflux. To this was added 1.89 g of NH4HCO2 (29.5 mmol, ~5 eq.) neat, at once. After 30 minutes, the reaction was cooled, filtered through solka floc, and the pad washed well with CHCl3. The solvents were removed in vacuo to yield a white solid which was partitioned between 2N NaOH and Et2O, the aqueous phase reextracted with Et2O, the combined Et2O phases dried (MgSO4), and the solvents removed to yield 1.46 g of crude free amine as an oil. This oil was dissolved in 300 mL of xylenes and heated at reflux with a Dean-Stark water separator for 48 hr. The solvents were removed in vacuo to yield a solid which was chromatographed on SiO2 eluting with 5% isopropylamine in MTBE to yield 1.03 g of 11-phenyl-2,3,6,11-tetrahydro-5H-imidazo[2,1-b][3]benzazepine free base (63%) as a white solid, mp 122°–123°. Treatment with the ethereal HCl provided the HCl salt, mp 252°–253°.

EXAMPLE 3

2,3,4,6,7,12-Hexahydro-12-phenylpyrimido[2,1 b][3]benzazepine (I: $R^1$=Ph, $R^2$=$R^3$=$R^4$=H, m=1, n=1)

A suspension of 10.0 g of the benzazepinone of Example 1 (42.1 mmol) in 100 mL of dry THF was cooled to 0° under N2 and treated dropwise with 18.5 mL of 2.5 M n-BuLi (46.4 mmol, 1.1 eq.) to produce a clear, pale yellow solution. After 30 minutes, 65 mL of DMPU was added dropwise, followed after an additional 30 minutes by 12.4 g of N-(3 bromopropyl)phthalimide (46.4 mmol), ~1.1 eq.) in 25 mL of THF added dropwise The reaction was allowed to warm to 25°, and maintained there for 24 hr. The resulting suspension was treated with 5 mL of saturated NH4Cl, then 75 mL of H2O. The suspension was filtered, and the solid washed well with H2O and placed in a vacuum oven. The filtrate was evaporated in vacuo, the residue extracted with Et2O (3×100 mL), and the combined Et2O layers washed with H2O, saturated NaCl, dried (MgSO4) and evaporated to yield 5.5 g of a semi-solid. This solid was triturated with Et20, filtered and the solid dried in a vacuum oven. Combined yield 13.7 g of phthalimidolactam (77%) as a white solid, mp 176°–177°.

To a suspension of 4.00 g of phthalimidolactam (9.44 mmol) in 50 mL of absolute EtOH at 25° was added 0.50 mL of H2NNH2·H2O (10.4 mmol, 1.1 eq.) and the mixture heated to reflux. After 2 hr, an additional 0.50 mL of H2NNH2·H2O (10.4 mmol, 1.1 eq.) was added. After a further 30 minutes at reflux, the reaction was cooled to 25°, filtered, and the solid washed with EtOH. The filtrate was evaporated to yield 3.3 g of crude free amine as a white solid, mp 104°–106°. A suspension of 3.2 g of this solid in 325 mL of xylenes was heated at reflux with a Dean-Stark water separator for 24 hr, cooled, and the solvents removed in vacuo to yield 3.0 of an oil which was chromatographed on SiO2 eluting with 10% isopropylamine in MTBE to provide 2.01 g of 2,3,4,6,7,12-hyxahydro-12-phenylpyrimido[2,1-b][3]benzazepine free base (77%) as a white, crystalline solid, mp 150°–152°. THF and ethereal HCl produce the HCl salt, mp 179°–180°.

EXAMPLE 4

5-Phenyl-1,3,4,5-tetrahydro-3(2H)-benzazepine-2-one (V: $R^3$=H, $R^4$=Ph)

To 250 mL of anhydrous absolute ethanol at 0° was added HCl(9) via bubbler for 10 minutes. To this solution was then added 9.5 g of 1,4-dihydro-1-phenyl-2(3H)-benzopyran-3-one (40.0 mmol) using 50 mL of ethanol to assist in the solid transfer. After one hour at 0°, the reaction was allowed to warm to 25° and maintained there for one hour. The solvents were removed in vacuo, and the residue azeotroped twice with CCl4 to give 11.5 g of ethyl 2-[(chloro)(phenyl)methyl]benzeneacetate (99%) as a colorless oil.

To a solution of 11.5 g of chloroester (40.0 mmol) in 150 mL of CH2Cl2 at 25° was added 6.89 mL of TMSCN (51.8 mmol, 1.3 eq.), followed by 1.17 mL of SnCl4 (9.8 mmol, ~0.25 eq.) dropwise After 2 hr at room temperature, the reaction mixture was poured onto 200 mL of ice and stirred until 25° was achieved. The solution was placed in a separatory funnel, the phases separated, and the aqueous phase reextracted with CH2Cl2. The combined CH2Cl2 layers were then washed with 5% NaHCO3, filtered through solka floc and dried (Na2SO4) to yield after solvent removal 10.1 g of ethyl 2-[(cyano)(phenyl)methyl]benzeneacetate.

To a suspension of 13.8 g of NaBH4 (358 mmol, 10 eq.) in 250 mL of THF at 25° was added 40.8 g trifluoroacetic acid (358 mmol, 10 eq.) dropwise over two hours, maintaining temperature below 30°. To this solution was then added 10.0 g of cyanoester (35.8 mmol, 1 eq.) in 70 mL of THF dropwise over 10 minutes. After three hours at 25°, the reaction mixture was diluted with 100 mL of Et2O and then treated extremely cautiously with 50 mL of H2O dropwise. The resulting suspension was transferred to a 2L Erlenmeyer flask and 100 mL of H2O followed by 50 mL of glacial HOAc were added with vigorous stirring. The resulting solution was evaporated in vacuo, and the residue partitioned between dilute NH4OH and Et2O. Reextraction of the aqueous phase with Et2O (2×250 mL), drying of the combined Et$_2$O phases (MgSO$_4$), and solvent removal provided 10.0 g of crude ethyl 2-(2-amino-1-phenylethyl)benzeneacetate as a yellow oil. This oil was dissolved immediately in PhCH$_3$, and refluxed for eight hours. Solvent removal and chromatography on silica gel (EtOAc eluent) provided 3.31 g (35%) of 5-phenyl-1,3,4,5-tetrahydro-3(2H)-benzazepine-2-one, mp 154°–155°.

EXAMPLE 5

3,6-Diphenyl-2,3,6,11-tetrahydro-5H-imidazo[2,1-b][3]benzazepine (I: R$^1$=R$^3$=H, R$^2$=R$^4$=Ph, n=0, m=1)

By a procedure analogous to that of Example 2, it is contemplated that 3,6-diphenyl-2,3,6,11-tetrahydro-5H-imidazo[2,1-b][3]benzazepine may be synthesized from 5-phenyl-1,3,4,5-tetrahydro-3(2H)-benzazepin-2-one of Example 4 and N,N-dibenzyl-$\beta$-chlorophenethylamine, available by benzylation of $\beta$-chlorophenethylamine of Barnett et al J. Chem. Soc. 1944, 94–96.

EXAMPLE 6

12-(3-Chlorophenyl)-2,3,4,6,7,12-hexahydro-10-methoxy-pyrimido[2,1-b][3]benzazepine (I: R$^1$=3-Cl-Ph, R$^2$=H, R$^3$=MeO, R$^4$=H, m=1, n=1)

By a procedure analogous to that of Examples 1 and 3, it is contemplated that 12-(3-chlorophenyl)-2,3,4,6,7,12-hexahydro-10-methoxypyrimido[2,1-b][3]benzazepine may be synthesized from p-methoxyphenethylamine and m-chloromandelic acid.

The compounds of this invention having formula I have antiarrhythmic activity as shown by the results of standard pharmacological tests carried out on representative examples as described below.

Antiarrhythmic activity was demonstrated by a procedure, which is a modification of standard programmed electrophysiological techniques utilized in large animals and in clinical studies in humans. Male Duncan-Hartley guinea pigs (600–800 grams) were anesthetized with sodium pentobarbital (30 mg/kg, i.p.) and artificially ventilated with a Harvard small-animal respirator. A left thoracotomy was performed and a fluid-filled catheter and transducer (Millar Micro-tip, Model 4F, Millar Inst. Inc., Houston, Tex.) were inserted through the anterior wall of the left ventricle to monitor left ventricular pressure (LvP). The first derivative of the LVP (dP/dt) was obtained from a Grass differentiator (Model 7P20B) and used as an index of contractile function. A lead II EKG along with LvP and dP/dt were continuously recorded on a Grass polygraph (Model 7B). Rate pressure product (RPP), an index of cardiac work, was calculated using peak systolic LVP and heart rate (HR).

Effective refractory periods (ERP) were evaluated during left ventricular pacing. Grass subcutaneous electrodes were implanted as bipolar ventricular electrodes to deliver stimuli from a Bloom DTU-2 stimulator (Bloom Electronics, Inc., Reading, Pa.) and stimulus isolation unit. Hearts were stimulated at the slowest frequency allowing consistent pacing (SI, 240–300 bpm) using 2 ms pulses at twice diastolic threshold. Threshold was determined by increasing the stimulation voltage until a 1:1 capture of the ventricular response with the stimulus was observed. A train of 8 normal pulses was delivered followed by a premature (S2) pulse. The interval between the last S1and the premature S2 pulse was reduced in 10-ms increments until a ventricular response was not initiated. The longest S1-S2 interval that failed to produce a ventricular response was defined as the ERP. Pacing stimuli and the EKG were displayed at a sampling frequency of 92 Hz on an Apple IIe microcomputer using a two-channel 8-bit A/D converter (R.C. Electronics, Compu-Scope APL-D2, Santa Barbara, Calif.).

Baseline hemodynamic function was evaluated followed by ventricular pacing to determine ERP. Pacing was discontinued prior to drug administration and resumed at set intervals during the protocol to evaluate ERP. Test compounds were administered (1 mL/kg) via the left ventricular catheter over a 15-second interval for doses less than 10 mg/kg. Higher doses (>10 mg/kg) were slowly infused over a 1-minute interval. Doses were cumulatively increased every 15 minutes until a maximally tolerated dose which reduced dP/dt by 50% was noted. Ten minutes after each dose, hemodynamics and ERP were reevaluated.

Data were analyzed using an analysis of variance for repeated measures of raw data and are expressed as means. An effective dose to increase ERP by a minimum of 20 msecs (ED$_{20}$), which was consistently a statistically significant increase, was derived for each animal from a linear regression of the data and expressed as a mean for the treated population. Biological significance was established at a probability of error less than 0.05. The results are presented in Table A.

TABLE A

| Example | ED$_{20}$ mg/kg |
|---------|-----------------|
| 2       | 0.3             |
| 3       | 0.3             |

The pharmaceutical compositions of the present invention include one or more of the compounds of this invention formulated into compositions together with one or more nontoxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, or parenterally (intravenously, intramuscularly or subcutaneously).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents for example sugars, sodium chloride and the like. Prolonged absorption of the injectable pharmaceutical form can be brought about by the use of agents delaying absorption; for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearat, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

We claim:
1. A compound of formula

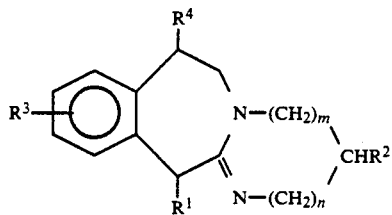

or an acid-addition salt thereof wherein
$R^1$ is phenyl, naphthyl, thienyl, phenyl substituted with one or two substituents chosen independently from the group consisting of lower-alkyl, lower-alkoxy and halogen, or $R^1$ is hydrogen when $R^4$ is phenyl or substituted phenyl;
$R^2$ is hydrogen or phenyl;
$R^3$ is one or two substituents chosen independently from the group consisting of hydrogen, lower-alkyl, lower-alkoxy and halogen;
$R^4$ is hydrogen; or, when $R^1$ is hydrogen, $R^4$ is phenyl or phenyl substituted with lower-alkyl, lower-alkoxy or halogen;
m and n are each zero, one or two and the sum of m plus n is one or two.

2. A compound according to claim 1 wherein m plus n is one.

3. A compound according to claim 2 wherein $R^1$ is phenyl or substituted phenyl and $R^2$ and $R^4$ are hydrogen.

4. 11-Phenyl-2,3,6,11-tetrahydro-5H-imidazo[2,1-b][3]benzazepine according to claim 3.

5. A compound according to claim 1 wherein m plus n is two.

6. A compound according to claim 5 wherein $R^1$ is phenyl or substituted phenyl and $R^2$ and $R^4$ are hydrogen.

7. 2,3,4,6,7,12-Hexahydro-12-phenylpyrimido[2,1-b][3]benzazepine according to claim 6.

8. A composition for the treatment of cardiac arrhythmia in a patient in need of such treatment which comprises a pharmaceutical carrier and an antiarrhythmically effective amount of a compound according to claim 1.

9. A composition for the treatment of cardiac arrhythmia in a patient in need of such treatment which comprises a pharmaceutical carrier and an antiarrhythmically effective amount of a compound according to claim 4.

10. A composition for the treatment of cardiac arrhythmia in a patient in need of such treatment which comprises a pharmaceutical carrier and an antiarrhythmically effective amount of a compound according to claim 7.

11. A method for the treatment of cardiac arrhythmia in a patient in need of such treatment which comprises the administration of an antiarrhythmically effective amount of a compound according to claim 1.

12. A method for the treatment of cardiac arrhythmia in a patient in need of such treatment which comprises the administration of an antiarrhythmically effective amount of a compound according to claim 4.

13. A method for the treatment of cardiac arrhythmia in a patient in need of such treatment which comprises the administration of an antiarrhythmically effective amount of a compound according to claim 7.

14. A process for preparing a compound according to claim 1 which comprises cyclizing a benzazepinone of formula

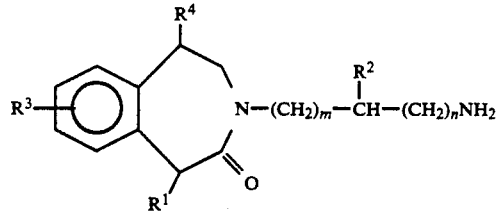

15. A method for the treatment of cardiac arrhythmia in a patient in need of such treatment which comprises the administration of a composition according to claim 8.

16. A method for the treatment of cardiac arrhythmia in a patient in need of such treatment which comprises the administration of a composition according to claim 9.

17. A method for the treatment of cardiac arrhythmia in a patient in need of such treatment which comprises the administration of a composition according to claim 10.

* * * * *